United States Patent

Herzig

(10) Patent No.: US 7,495,119 B2
(45) Date of Patent: Feb. 24, 2009

(54) PROCESS FOR PREPARING β-KETOCARBONYL-FUNCTIONAL ORGANOSILICON COMPOUNDS

(75) Inventor: Christian Herzig, Waging am See (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/743,687

(22) Filed: May 3, 2007

(65) Prior Publication Data

US 2007/0260081 A1    Nov. 8, 2007

(30) Foreign Application Priority Data

May 4, 2006    (DE) ................. 10 2006 020 815

(51) Int. Cl.
*C07F 7/10*    (2006.01)

(52) U.S. Cl. .................................................. 556/419

(58) Field of Classification Search .................. None
See application file for complete search history.

(56) References Cited

U.S. PATENT DOCUMENTS

| 4,808,649 A | 2/1989 | Gay et al. |
| 4,861,839 A | 8/1989 | Mizuguchi et al. |
| 5,952,443 A | 9/1999 | Wilt et al. |
| 6,121,404 A | 9/2000 | Liles |

FOREIGN PATENT DOCUMENTS

WO    2007060089 A2    5/2007

OTHER PUBLICATIONS

English Abstract corresponding to WO 2007/060089 A.

*Primary Examiner*—Samuel A Barts
(74) *Attorney, Agent, or Firm*—Brooks Kushman P.C.

(57) ABSTRACT

β-ketocarbonyl-functional organosilicon compounds are prepared by reacting, organosilicon compounds containing an SiC-bonded organic radical having a primary amino group, with
organic ester compounds containing a group of the formula

—O—C(=O)— and, reacting the product with diketenes or diketene derivatives, to produce β-ketocarbonyl-functional organosilicon compounds containing at least one SiC-bonded radical of the formulae —R$^1${—N[C(=O)—CHR$^5$—C(=O)—CH$_2$R$^5$]—R$^1$}$_x$—NH—C(=O)—(O)$_v$—R$^4${—O—[C(=O)—CHR$^5$—C(=O)—CHR$^5$]$_y$H}$_z$ or —R$^1$(—NR$^{2'}$—R$^1$)$_x$—NH—C(=O)—(O)$_v$—R$^4${—O—[C(=O)—CHR$^5$—C(=O)—CHR$_5$]$_y$H}$_z$ R$^1$ is a divalent C$_{1-18}$ organic radical
R$^2$ is a hydrogen atom or a monovalent C$_{1-18}$ organic radical,
R$^5$ is hydrogen,
v is 1,
x is 0 or an integer from 1 to 10,
R$^{2'}$ has one of the meanings of R$^2$ with the proviso that R$^{2'}$ is not a hydrogen atom, y is 0 or 1, and z is 1 or 2.

8 Claims, No Drawings

PROCESS FOR PREPARING β-KETOCARBONYL-FUNCTIONAL ORGANOSILICON COMPOUNDS

BACKGROUND OF THE INVENTION

1. Field of the Invention

The invention relates to a process for preparing β-ketocarbonyl-functional organosilicon compounds. The invention further relates to β-ketocarbonyl-functional organosilicon compounds prepared thereby.

2. Background Art

U.S. Pat. No. 4,861,839 describes alkoxysilanes which are substituted by acetoacetic (thio)ester or acetoacetamido groups and are used as monomeric chelating ligands for metal catalysts.

Polymeric β-keto ester siloxanes are known from U.S. Pat. No. 4,808,649, which also discloses a process for preparing them, and their use as stabilizers for polyvinyl chloride.

Functional polysiloxanes containing acetoacetate groups are described in U.S. Pat. No. 5,952,443, wherein part of the functional groups must contain at least two β-ketocarbonyl groups per functional group, and the number of dimethylsiloxy units is not greater than 50. Crosslinking by means of polyamines in surface coating formulations is described.

The modification of carbinol or amino polysiloxanes by means of diketene and its derivatives is described in U.S. Pat. Ser. No. 6,121,404. The products are used in aqueous solution together with amino polysiloxanes for producing elastomer films.

SUMMARY OF THE INVENTION

It is an object of the invention to provide a process for preparing β-ketocarbonyl-functional organosilicon compounds in which ungelled products are obtained. These and other objects are achieved by the invention, wherein primary amino group-functional organosilicon compounds are reacted with an organic ester compound.

DETAILED DESCRIPTION OF THE PREFERRED EMBODIMENT(S)

The invention thus provides a process for preparing β-ketocarbonyl-functional organosilicon compounds, wherein, in a 1st step, (1) organosilicon compounds containing at least one SiC-bonded organic radical having a primary amino group, are reacted with (2) organic ester compounds, preferably cyclic organic carbonates and lactones, containing a group of the formula

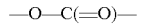

and, in a 2nd step the reaction products of (1) and (2) obtained in the 1st step are subsequently reacted with (3) diketenes or diketene derivatives.

As organosilicon compounds (1), preference is given to using those which contain at least one SiC-bonded organic radical A of the general formula $$-R^1(-NR^2-R^1)_x-NH_2 \qquad (I),$$

where

R$^1$ is a divalent organic radical having from 1 to 18 carbon atoms, preferably a divalent hydrocarbon radical having from 1 to 18 carbon atoms, R$^2$ is a hydrogen atom or a monovalent organic radical having from 1 to 18 carbon atoms, preferably a hydrogen atom or a monovalent hydrocarbon radical having from 1 to 18 carbon atoms, more preferably a hydrogen atom, x is 0 or an integer from 1 to 10, preferably 0, 1 or 2.

The organosilicon compounds (1) can be monomeric, oligomeric or polymeric and can have a linear, branched or cyclic structure. The organosilicon compounds are more preferably organopolysiloxanes comprising units of the general formula

where

A is as defined above,

R is a monovalent, substituted or unsubstituted hydrocarbon radical having from 1 to 18 carbon atoms per radical, R$^3$ is a hydrogen atom or an alkyl radical having from 1 to 8 carbon atoms, preferably a hydrogen atom or a methyl or ethyl radical, a is 0 or 1, b is 0, 1, 2 or 3 and c is 0 or 1, with the proviso that the sum a+b+c is ≦3 and on average at least one radical A is present per molecule.

Preferred examples of organosilicon compounds (1) are organopolysiloxanes of the general formulae

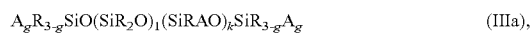

and

where A, R and R$^3$ are as defined above, g is 0 or 1, k is 0 or an integer from 1 to 30 and l is 0 or an integer from 1 to 1000, m is an integer from 1 to 30 and n is 0 or an integer from 1 to 1000, with the proviso that on average at least one radical A is present per molecule.

Examples of radicals R are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as n-heptyl radical, octyl radicals such as the n-octyl radical and isooctyl radicals such as 2,2,4-trimethylpentyl radical, nonyl radicals such as the n-nonyl radical, decyl radicals such as the n-decyl radical, dodecyl radicals such as the n-dodecyl radical and octadecyl radicals such as the n-octadecyl radical; cycloalkyl radicals such as cyclopentyl, cyclohexyl, cycloheptyl and methylcyclohexyl radicals; alkenyl radicals such as the vinyl, 5-hexenyl, cyclohexenyl, 1-propenyl, allyl, 3-butenyl and 4-pentenyl radical; alkynyl radicals such as the ethynyl, propargyl and 1-propynyl radical; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, and the α- and β-phenylethyl radicals.

Examples of radicals R$^1$ are alkylene radicals having from 1 to 18 carbon atoms, e.g. radicals of the formulae $-CH_2-$, $-CH_2CH_2-$, $-CH(CH_3)-$,
$-CH_2CH_2CH_2-$, $-CH_2C(CH_3)H-$,
$-CH_2CH_2CH_2CH_2-$, $-CH_2CH_2CH(CH_3)-$,
with preference being given to $-CH_2CH_2-$ and
$-CH_2CH_2CH_2-$.

Examples of radicals A are $-CH_2-NH_2$, $-CH(CH_3)-NH_2$, $-C(CH_3)_2-NH_2$,
$-CH_2CH_2-NH_2$, $-CH_2CH_2CH_2-NH_2$,
$-CH_2CH_2CH_2CH_2-NH_2$, $-CH_2CH_2CH(CH_3)-NH_2$, $-CH_2CH_2CH_2-NH-$
$CH_2CH_2-NH_2$, $-CH_2CH_2CH_2-N(CH_3)-$
$CH_2CH_2-NH_2$, $-CH_2CH_2CH_2[-NH-$
$CH_2CH_2]_2-NH_2$, and $-CH_2CH_2C(CH_3)_2$
$CH_2-NH_2$.

The examples of hydrocarbon radicals previously disclosed as R are also suitable for hydrocarbon radicals $R^2$.

Examples of alkyl radicals $R^3$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical.

The organosilicon compounds (1) employed in the invention preferably have a viscosity of from 1 mPa.s to 1,000,000 mPa.s at 25° C., more preferably from 100 mPa.s to 50,000 mPa.s at 25° C., and preferably have a molecular weight $M_n$ of preferably from 200 to 200,000 Daltons (Da), more preferably from 2000 to 50,000 Da.

The organosilicon compounds (1) contain primary, and optionally secondary amino groups, in titratable amounts of from 0.01 to 12 meq/g of meq/g organosilicon compound (1), more preferably in the range from 0.05 to 3 meq/g of organosilicon compound (1). In this and other respects, it is possible to use one type of organosilicon compound (1) or a plurality of types of organosilicon compounds (1) in the process.

The organic ester compounds (2) preferably contain a group of the formula $-O-C(=O)-$. Preference is given to using lactones or cyclocarbonates of the general formula $$(O)_v-R^4-O-C=O, \quad (OH)_{z-1} \quad (V)$$

where $R^4$ is a divalent or trivalent hydrocarbon radical which has from 1 to 18 carbon atoms and is optionally interrupted by one or more separate oxygen atoms, preferably a divalent hydrocarbon radical having from 1 to 5 carbon atoms,
v is 0 or 1, preferably 1, and
z is 1 or 2, preferably 1.

Examples of divalent radicals $R^4$ having v=0 and z=1 in formula (V), i.e. lactones, are those of the formulae
$-CH_2CH_2-$, $-CH_2CH_2CH_2-$, $-CH_2CH_2CH_2CH_2-$
and $-CH_2CH_2CH_2CH_2CH_2-$.

Examples of divalent radicals $R^4$ having v=1 and z=1 in formula (V), i.e. cyclocarbonates, are those of the formulae
$-CH_2CH_2-$, $-CH_2CH_2CH_2-$, $-CH_2CH(CH_3)-$ and $-CH(CH_3)CH_2-$, and examples of trivalent radicals $R^4$ having v=1 and z=2 in formula (V), i.e. when radicals $R^4$ are substituted by a hydroxyl group, are those of the formulae $-CH_2CH(CH_2-)-$ and $-CH(CH_2-)CH_2-$.

Examples of organic ester compounds (2) are propiolactone, butyrolactone, caprolactone, ethylene carbonate, propylene carbonate, butylene carbonate and glyceryl carbonate. In principle, it is also possible to use open-chain esters such as alkyl esters of hydroxy acids for the reaction of organosilicon compounds (1), but the cyclic esters are preferred over these, with cyclocarbonates being particularly preferred.

The ester compounds (2) are preferably used in an approximately stoichiometric amount based on the sum of all primary amino groups which are present in (1). Ester compounds (2) are therefore preferably used in amounts of from 1.0 to 2.0 mol, more preferably from 1.0 to 1.2 mol, per mol of primary amino group $-NH_2$ in organosilicon compounds (1).

The 1st step of the process of the invention, e.g. the reaction of (1) with (2), is preferably carried out at a temperature of from 10° C. to 120° C., more preferably from 25° C. to 80° C. When the ester compounds (2) are insoluble or only sparingly soluble in the organosilicon compounds (1), a higher reaction temperature of from 50° C. to 100° C. is preferred. The progress of the reaction in the 1st step of the process of the invention can generally be visualized by the clarification of an initially turbid mixture.

The reaction products of (1) and (2) obtained in the 1st step are preferably organosilicon compounds which contain at least one SiC-bonded organic radical B of the general formula $$-R^1(-NR^2-R^1)_x-NH-C(=O)-(O)_v-R^4 \quad (VI),$$
$$(-OH)_z$$

where $R^1$, $R^2$, $R^4$, v and x are as defined above and z is 1 or 2, preferably 1. As a result of the reaction of (1) with (2), the radical B contains urethane carbinol groups.

In the 2nd step of the process of the invention, diketenes of the general formula $$R^5-CH=C\underset{O}{\overset{H}{\diagdown}}\underset{}{\overset{R^5}{\diagup}}C=O, \quad (VII)$$

where
$R^5$ is a hydrogen atom or a hydrocarbon radical having from 1 to 18 carbon atoms, preferably a hydrogen atom, are used as diketenes (3). Examples of hydrocarbon radicals R are also examples of hydrocarbon radicals $R^5$.

Preference is given to using diketene of the formula $$CH_2=C\underset{O}{\overset{CH_2}{\diagdown}}\underset{}{\diagup}C=O$$

It is also possible to use diketene derivatives such as a diketene-acetone adduct or t-butyl acetoacetate, which liberate diketene at elevated temperatures.

In the 2nd step of the process, the amount of diketenes (3) with which the reaction products of (1) and (2) are reacted can be selected within a wide range. When the organosilicon compounds (1) contain not only primary amino groups but also secondary amino groups, amounts of diketenes (3) which are at least equivalent to these primary and secondary amino groups are preferably used.

The carbinol groups formed by the reaction of (1) with (2) can be reacted completely or partly with diketenes (3). For this purpose, it can be advantageous to use a slight excess of diketenes (3) which, after the reaction is complete, are preferably removed under reduced pressure (volatile diketene) or removably reacted. Diketenes (3) are therefore preferably used in amounts of from 0.5 to 1.25 mol, more preferably from 0.8 to 1.1 mol, per mol of the sum of secondary amino groups (secondary —NH—) and carbinol group in the reaction products of (1) and (2) in the 2nd step of the process of the invention.

A particular embodiment of the invention comprises the equimolar use of diketene and amino and carbinol groups, i.e. diketene (3) is preferably used in amounts of about 1.0 mol per mol of secondary amino groups and carbinol groups in the reaction products of (1) and (2).

In the 2nd step of the process, the reaction of diketenes (3) with the secondary amino groups in the reaction product of (1) with (2) preferably proceeds spontaneously at ambient temperature, but can also be carried out at elevated temperatures. However, as elevated temperature is necessary to react the urethane carbinol groups in the reaction product of (1) and (2) with diketenes (3), the reaction is therefore preferably carried out at a temperature of from 50° C. to 120° C.

The reaction with diketenes (3) in the 2nd step of the process is preferably carried out in the presence of basic catalysts such as tertiary amines. Examples of tertiary amines are triethylamine, trinonylamine, tris(isotridecylamine), diazabicyclooctane, tetramethylethylenediamine, pentamethyldiethylenetriamine, pentamethyldipropylenetriamine and bis(dimethylaminopropyl)aminoethanol.

The process is preferably carried out at the pressure of the surrounding atmosphere, i.e. at about 1020 hPa, but it can also be carried out at higher or lower pressures, and can be carried out batchwise, semicontinuously or continuously.

The preparation of the β-ketocarbonyl-functional organosilicon compounds can be conducted in organic solvents, which can be particularly advantageous particularly when the organosilicon compounds have high viscosities. Examples of solvents are saturated hydrocarbons such as n-pentane, n-hexane, n-heptane and n-octane and their branched isomers, petroleum spirits, e.g. alkane mixtures having a boiling range from 80° C. to 140° C. at 1020 hPa; unsaturated hydrocarbons such as 1-hexene, 1-heptene, 1-octene and 1-decene; aromatic hydrocarbons such as benzene, toluene and xylene(s); halogenated alkanes having from 1 to 6 carbon atom(s), e.g. methylene chloride, trichloroethylene and perchloroethylene; ethers such as di-n-butyl ether; alcohols such as methanol, ethanol, n-propanol and isopropanol; and low molecular weight linear and cyclic organopolysiloxanes.

When $R^2$ is hydrogen in the organosilicon compounds (1), the reaction products obtained in the process of the invention are preferably β-ketocarbonyl-functional organosilicon compounds containing at least one SiC-bonded organic radical $G^1$ of the general formula

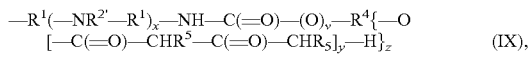    (VIII), where
$R^1$, $R^4$, $R^5$, v and x are as defined above,
y is 0 or 1, preferably 1,
z is 1 or 2, preferably 1, with the proviso that y is 1 in at least one part of the β-ketocarbonyl-functional organosilicon compounds.

When $R^2$ is not a hydrogen atom but instead an organic radical having from 1 to 18 carbon atoms in the organosilicon compounds (1), the reaction products obtained in the process of the invention are preferably β-ketocarbonyl-functional organosilicon compounds containing at least one SiC-bonded organic radical $G^2$ of the general formula —$R^1$(—$NR^{2'}$—$R^1$)$_x$—NH—C(=O)—(O)$_v$—$R^4${—O
[—C(=O)—CHR$^5$—C(=O)—CHR$_5$]$_y$—H}$_z$    (IX), where
$R^1$, $R^4$, $R^5$, v, x, y and z are as defined above,
$R^{2'}$ has one of the meanings of $R^2$ with the proviso that $R^{2'}$ is not a hydrogen atom, and with the proviso that y is 1 in at least one part of the β-ketocarbonyl-functional organosilicon compounds.

Examples of radicals $R^2$ apply in their full scope to radicals $R^{2'}$ except that $R^{2'}$, in this context, is not a hydrogen atom. Preference is given to y being 1 in at least 80 mol %, preferably at least 90 mol %, of the β-ketocarbonyl-functional organosilicon compounds.

The reaction products obtained are preferably β-ketocarbonyl-functional organopolysiloxanes comprising units of the general formula $$G_a R_b (OR^3)_c SiO_{\frac{4-(a+b+c)}{2}},$$    (X)

where
G is a radical selected from the group consisting of radicals $G^1$ and $G^2$,
where $G^1$ and $G^2$ are as defined above, and
R, $R^3$, a, b and c are as defined above, with the proviso that the sum a+b+c is ≦3 and on average at least one radical G is present per molecule.

Preferred examples of β-ketocarbonyl-functional organopolysiloxanes are organopolysiloxanes of the general formulae $G_g R_{3-g} SiO(SiR_2O)_l (SiRGO)_k SiR_{3-g} G_g$    (IIIa), and $(R^3O)R_2 SiO(SiR_2O)_n (SiRGO)_m SiR_2(OR^3)$    (IIIb), where G, R and $R^3$ are as defined above,
g is 0 or 1,
k is 0 or an integer from 1 to 30 and
l is 0 or an integer from 1 to 1000,
m is an integer from 1 to 30, and
n is 0 or an integer from 1 to 1000, with the proviso that on average at least one radical G is present per molecule.

The β-ketocarbonyl-functional organosilicon compounds obtained by the process of the invention have a molecular weight $M_n$ of preferably from 400 to 200,000 daltons, preferably from 2000 to 100,000 daltons.

EXAMPLES

Example 1

200 g of an α,ω-bis(aminopropyl)polydimethylsiloxane having a content of primary amino groups of 0.353 meq/g are stirred together with 8.08 g of ethylene carbonate at 70° C. for 3 hours, with the initially turbid mixture becoming clear. At the same temperature, 5.94 g of diketene, corresponding to the amount of the primary amino groups used, are then added. The reaction mixture is then catalyzed by means of 0.04 g of a 10% strength solution of diazabicyclooctane in diethylene glycol monobutyl ether. The acetoacetylation commences with slight evolution of heat. After a further 2 hours, no diketene can be detected in the IR spectrum. The reaction mixture is cooled. This gives a clear, yellowish oil having a viscosity of 554 mm²/s (25° C.). Amino groups can no longer be detected (<0.001 meq/g). The ¹H-NMR spectrum confirms the quantitative formation of acetylacetoxyethylurethane groups. The product contains about 0.8% by weight of unconsumed ethylene carbonate, which can be removed at 120° C. under reduced pressure.

Example 2

200 g of a copolymer of aminoethylaminopropylmethylsiloxy and dimethylsiloxy units having predominantly methoxy end groups and a total amine content of 0.297 meq/g and a viscosity of 1120 mm²/s (25° C.) together with 2.62 g of ethylene carbonate are maintained at 80° C. for 2 hours while stirring well. The initially milky reaction mixture becomes clear. An ¹H-NMR spectrum of the intermediate shows quantitative conversion of the primary amino groups into 2-hydroxyethylurethane groups. 4.99 g of diketene, corresponding to an equimolar amount based on the sum of carbinol and secondary amino groups, are then added, whereupon an exothermic reaction commences quickly. 0.04 g of a 10% strength solution of diazabicyclooctane in diethylene glycol monobutyl ether is then added and the mixture is stirred at 80° C. for a further 2 hours, after which all of the diketene has been consumed. Cooling of the mixture gives a colorless, clear oil having a viscosity of 30,500 mm²/s (25° C.) and a titratable residual amine content of 0.002 mequ./g.

Comparative Experiment:

The procedure of Example 2 is repeated with the modification that the 1st step of the process, viz. the reaction with ethylene carbonate, is not carried out. After introduction of diketene, the previously mobile oil gels after less than 1 minute.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing β-ketocarbonyl-functional organosilicon compounds, comprising reacting,
   (1) organosilicon compounds containing an SiC-bonded organic radical having a primary amino group with
   (2) at least one lactone or cyclocarbonate of the formula

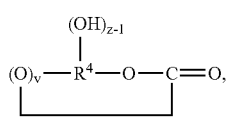

(V)

where $R^4$ is a divalent or trivalent hydrocarbon radical which has from 1 to 18 carbon atoms and is optionally interrupted by one or more separate oxygen atoms,
   v is 0 or 1, and
   z is 1 or 2,
   and, in a 2nd step
the reaction products of (1) with (2) thus obtained are subsequently reacted with (3) diketenes or diketene derivatives.

2. The process of claim 1, wherein organosilicon compound(s) containing at least one SiC-bonded organic radical A of the formula

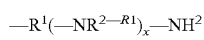

(I), where
   $R^1$ is a divalent organic radical having from 1 to 18 carbon atoms,
   $R^2$ is a hydrogen atom or a monovalent organic radical having from 1 to 18 carbon atoms,
   x is 0 or an integer from 1 to 10, preferably 0, 1 or 2, are used as organosilicon compounds (1).

3. The process of claim 1, wherein organopolysiloxane(s) comprising units of the formula

(II)

where
   R is a monovalent, substituted or unsubstituted hydrocarbon radical having from 1 to 18 carbon atoms per radical,
   $R^3$ is a hydrogen atom or an alkyl radical having from 1 to 8 carbon atoms,
   a is 0 or 1,
   b is 0, 1, 2 or 3 and
   c is 0 or 1,
with the proviso that the sum a+b+c is ≦3 and on average at least one radical A is present per molecule,
   are used as organosilicon compounds (1).

4. The process of claim 1, wherein organopolysiloxane(s) of the formulae

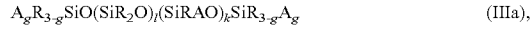

(IIIa), or

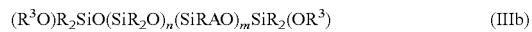

(IIIb)

where
   g is 0 or 1,
   k is 0 or an integer from 1 to 30, and
   l is 0 or an integer from 1 to 1000,
   m is an integer from 1 to 30, and
   n is 0 or an integer from 1 to 1000,
   with the proviso that on average at least one radical A is present per molecule,
are used as organosilicon compounds (1).

5. The process of claim 1, wherein diketenes of the general formula

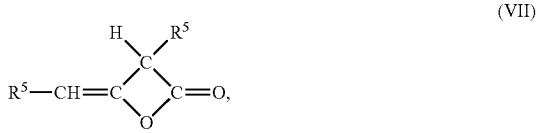

(VII)

where
   $R^5$ is a hydrogen atom or a hydrocarbon radical having from 1 to 18 carbon atoms, are used as diketenes (3).

6. The process of claim 1, wherein a cyclocarbonate is employed.

7. The process of claim 6, wherein the cyclocarbonate is at least one selected form the group consisting of ethylene carbonate, propylene carbonate, butylene carbonate, and glyceryl carbonate.

8. The process of claim 6, wherein the cyclocarbonate comprises ethylene carbonate.

* * * * *

UNITED STATES PATENT AND TRADEMARK OFFICE
CERTIFICATE OF CORRECTION

PATENT NO. : 7,495,119 B2
APPLICATION NO. : 11/743687
DATED : February 24, 2009
INVENTOR(S) : Christian Herzig It is certified that error appears in the above-identified patent and that said Letters Patent is hereby corrected as shown below:

Column 7, Line 64, Claim 2:

Delete:

"-$R^1$(-$NR^2$-$R^1$)$_x$-$NH^2$      (I),"

And insert:

-- -$R^1$(-$NR^2$-$R^1$)$_x$-$NH_2$      (I), --

Signed and Sealed this

Twenty-first Day of April, 2009

JOHN DOLL
*Acting Director of the United States Patent and Trademark Office*